United States Patent [19]

Takahashi

[11] Patent Number: 4,693,644

[45] Date of Patent: Sep. 15, 1987

[54] ANNULAR HOLE CUTTER

[75] Inventor: Shiro Takahashi, Tokyo, Japan

[73] Assignee: Man Design Co., Ltd., Tokyo, Japan

[21] Appl. No.: 875,456

[22] Filed: Jun. 18, 1986

Related U.S. Application Data

[63] Continuation of Ser. No. 589,416, Mar. 14, 1984, abandoned.

[30] Foreign Application Priority Data

Mar. 14, 1983 [JP] Japan ............................ 58-36494[U]

[51] Int. Cl.$^4$ ............................................. B23B 51/04
[52] U.S. Cl. .................................... 408/204; 408/207; 408/703
[58] Field of Search ............... 408/204, 206, 207, 209, 408/703, 705, 67

[56] References Cited

U.S. PATENT DOCUMENTS

| | | | |
|---|---|---|---|
| 2,996,061 | 8/1961 | Miller | 408/57 |
| 3,227,013 | 1/1966 | Zimmermann | 408/204 |
| 3,592,554 | 7/1971 | Takahara | 408/204 |
| 3,609,056 | 9/1971 | Hougen | 408/204 |
| 4,322,187 | 3/1982 | Hougen | 408/204 |
| 4,406,334 | 9/1983 | Baumann et al. | 408/204 |

FOREIGN PATENT DOCUMENTS 25983 3/1978 Japan .................................... 408/204

Primary Examiner—Gil Weidenfeld
Assistant Examiner—Daniel W. Howell
Attorney, Agent, or Firm—Birch, Stewart, Kolasch & Birch

[57] ABSTRACT

An annular hole cutter including a barrel and cutting teeth attached to a lower portion of the barrel. A portion of a cutting edge of the cutting teeth including hard teeth each having an outer cutting edge formed into a segment which is concentric with respect to an outer circumferential surface of the barrel and an inner cutting edge formed into a segment which is eccentric a slight distance with respect to an inner circumferential surface of the barrel in the radial direction. Eccentric regions of the hard tooth project from the inner circumference of the barrel in the centripetal direction. A gullet is defined between adjacent edges of the cutting teeth for the removal of chips. An inner peripheral surface of the hard teeth located above a stepped portion of the gullets each being formed into a segment which is concentric with respect to the inner circumferential surface of the barrel, and has the same radius of curvature as that of the inner circumferential surface.

3 Claims, 4 Drawing Figures

4,693,644

ANNULAR HOLE CUTTER

This is a continuation of application Ser. No. 589,416, filed Mar. 14, 1984 and now abandoned.

FIELD OF THE INVENTION

The present invention relates to an annular hole cutter designed to cut an annular groove in a workpiece to form a round hole in the workpiece.

BACKGROUND OF THE INVENTION

Annular cutters of the type which include a barrel in a cylindrical form and cutting teeth attached at regular intervals to the lower portion of a housing are disclosed in Japanese Utility Model Kokai Publication Nos. 57-100415 (1982) and 57-100416 (1982). The cutting teeth are partly formed of a hard material. A groove is defined between the adjacent teeth for the removal of chips. The annular cutter is designed to form a hole in the workpiece by allowing a cylindrical slug to drop through. Such a type of annular hole cutter can cut a hole larger than that formed by a twist cutter, since the hole-cutting or drilling is effected while drilling an annular hole having a width corresponding to the thickness of the hard teeth. Furthermore, since the cutting area of the cutting teeth is reduced by dividing the cutting teeth into several groups, smaller resistance to cutting and faster cutting speed are achieved.

A problem is involved in the use of the above described annular cutter. More specifically, the deeper the depth of the hole being cut, the more difficult the removal of chips. For that reason, minute chips tend to be jammed or wedged in between the inner portions of the cutting teeth and a cylindrical core formed during drilling. The core drops off as a slug after the completion of the drilling. A representative slug 14 is illustrated in FIG. 4. When jamming of chips becomes significant, there is an increase in the resistance to cutting, which may eventually lead to break-down of the annular cutter. Alternatively, there is an increase in the load applied to an electric motor for driving the cutter, which may ultimately result in burning-out of the motor. In some cases, the heat of friction generated by an increase in the resistance to cutting may give rise to a melting of the chips. The chips are in turn deposited and cured onto the inner cutting teeth. As a consequence, the cutting edges will chip or break down, or burning-out of the motor will take place.

SUMMARY OF THE INVENTION

The present invention has for its main object to prevent jamming of chips during hole-cutting. The invention is characterized in that the hard teeth attached to cutting teeth are divided into two segments, one being concentric and the other being eccentric with respect to the inner circumference of a barrel of the cylindrical form. Within the barrel, the inner teeth of the hard teeth are configured to follow the same curved surface as that of the inner circumference of the barrel.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Referring to FIGS. 1-4 inclusive, an annular hole cutter includes a cylindrical barrel 1 and is provided with a shank 2 at the center of the upper end thereof. As is the case with a conventional cutter, the shank 2 is mounted on an arbor (not illustrated) and hole-cutting or drilling is effected around the axis A—A of the shank 2. The barrel 1 includes an outer circumferential surface 3 and an inner circumferential surface 4.

Figure 1:
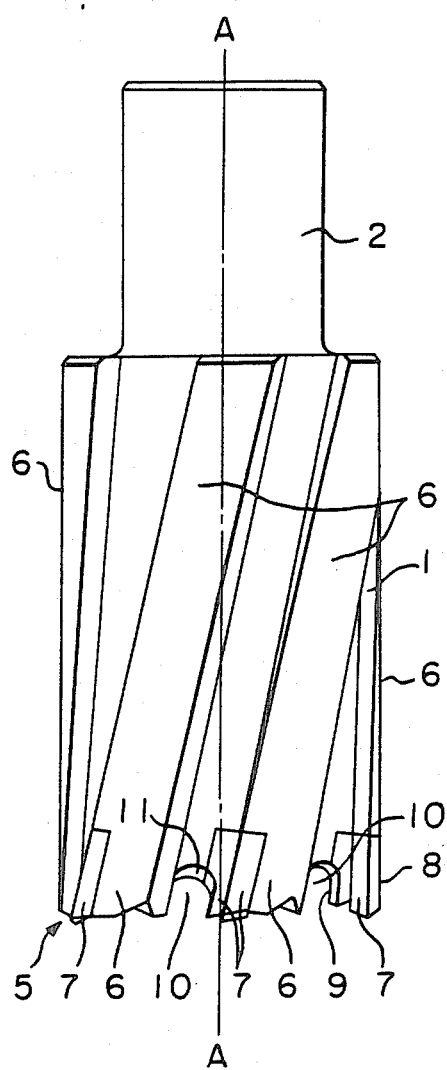
FIG. 1 is a front view showing one embodiment of the present invention.

As generally indicated, downwardly projecting cutting teeth 5 are mounted on the lower portion of the barrel 1 at regular intervals. In the embodiment illustrated, five (5) cutting teeth are provided. However, it is to be noted that the number of cutting teeth is determined depending upon the diameter of the barrel 1, the material from which the teeth are formed, etc. As shown in FIGs. 1, lands 6 extend upwardly of the teeth 5 at a given angle of convolution in a gently spiral fashion.

Figure 2:
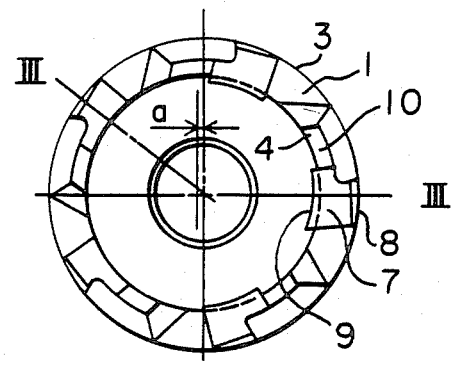
FIG. 2 is a bottom view of the embodiment illustrated in FIG. 1.
Figure 3:
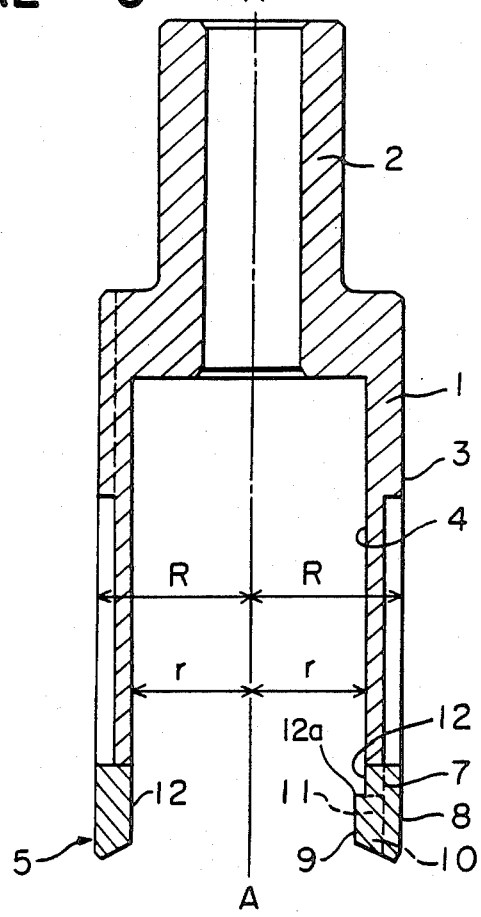
FIG. 3 is an end view sectioned along the line III—III of FIG. 3.

As illustrated in FIG. 3, the outer and inner circumferential surfaces 3 and 4 of the barrel 1 are formed into concentric circles of radii R and r relative to the axis A—A of the shank 2. As shown in FIGS. 2 and 3, the cutting teeth include outer cutting edges 8 each formed into a segment which is in concentric relation to the outer circumferential surface 3, and inner cutting edges 9 each being ecentric a slight distance a with respect to the inner circumferential surface 4 from the axis A—A in the radial direction. The inner cutting edges 9 project at the eccentric positions from the inner circumferential surface 4 of the barrel 1 in the centripetal direction. The outer and inner cutting edges 8 and 9 are both formed of super-hard steel, and are hereinafter referred to as the hard teeth 7.

A gullet 10 is provided between the adjacent edges of the cutting teeth 5 for the removal of chips. Chips produced by the inner cutting edges 9 are usually discharged through the gullets 10 to the outside along the lands 6. However, according to the annular hole cutter of the present invention, the inner periphery of a portion of each hard tooth 7 located above the top wall of each gullet 10 is formed into a segment having a radius equal to the radius r of the inner circumferential surface 4 of the barrel 1. An inner peripherial surface 12 of all the hard teeth 7 is configured to the inner circumferential surface 4 of the barrel 1, so that there is no step defined between the inner circumferential surface 4 of the barrel 1 and the inner peripherial surface 12 of the inner cutting edges 9 while there is a step or shoulder 12a (see FIG. 3) formed above the top surface 11 of the gullet 10 between the inner peripheral surface 12 of the upper portion of each inner cutting edge 9 and the inner peripheral surface of the lower portion of the inner cutting edge 9.

Figure 4:
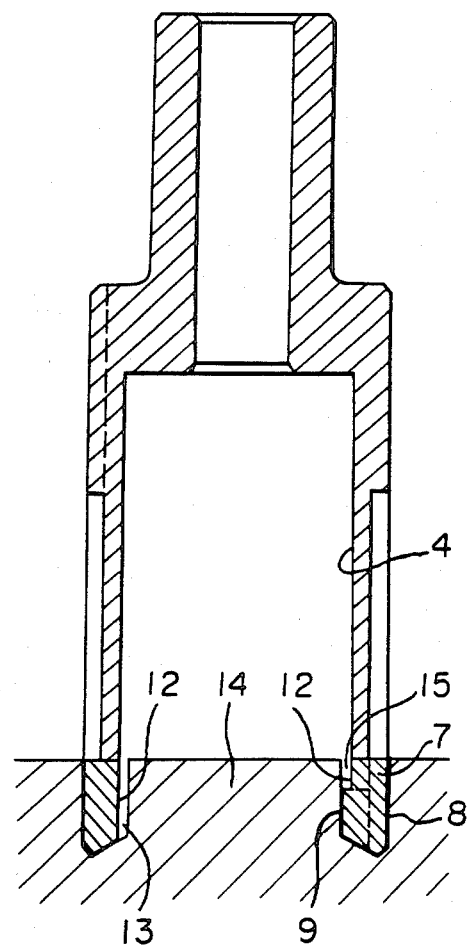
FIG. 4 is a view illustrating the embodiment of the present invention in use.

In operation, when the electric motor is actuated after the shank 2 has been supported by the cutter arbor, the cutting teeth 5 attached to the lower portion of the barrel 1 initiate cutting. As shown in FIG. 4, an annular groove 13 is then formed by the hard, outer and inner cutting edges 8 and 9 forming a part of the cutting teeth 5. During cutting since the hard, inner cutting edges 9 are eccentric, chips produced by cutting with the inner cutting edges 9 pass between the inner cutting edges 9 and a core 14 which is being gradually formed and are discharged through the gullets 10 along the lands 6 formed on the barrel 1. In this case, even though a portion of the chips are not discharged from the gullets 10, and ascend along the inner circumference 4 of the barrel 1, it is very unlikely that such chips will be jammed or wedged in between the inner periphery of the inner cutting edges 9 and the core 14. The chips are permitted to enter a gap 15 corresponding to the degree of eccentricity, which is formed between the inner peripherial surface 12 of the inner cutting edges 9 and the core 14, as shown in FIG. 4. This occurs because the inner peripherial surface 12 of the hard, inner cutting edges 9 located above the steps 12a are formed in the same curved surface as the inner circumferential surface 4 of the barrel 1.

After completion of the drilling, the slug drops off through a gap between the lower portion (the edge side) and the inner peripheral surface or upper portion 12 of the eccentric inner cutting edges 9.

As mentioned above, the present invention provides an annular hole cutter including a barrel 1 in a cylindrical form and cutting teeth 5 attached to the lower portion of said barrel. A portion of the cutting edges of said cutting teeth is formed of hard teeth 7 each including an outer cutting edge 8 formed into a segment which is concentric with respect to the outer circumferential surface 3 of said barrel and an inner cutting edge 9 formed in a segment which is eccentric a slight distance with respect to the inner circumferential surface 4 of said barrel in the radial direction. The eccentric regions 9 of the hard teeth project from the inner circumferential surface of said barrel in the centripetal direction. A gullet 10 is provided for the removal of chips and is defined between the adjacent edges of said cutting teeth 5. The inner peripheral surface 12 of the hard teeth located above the steps 12a of said gullets are each formed into a segment which is concentric with respect to the inner circumferential surface 4 of said barrels, and has the same radius of curvature as that of said inner circumference.

With the annular cutter of the present invention, a more sharper cutting is achieved than with a conventional cutter using concentric teeth due to the presence of the eccentric inner cutting edges of the hard teeth. In addition, the upper inner peripheries of the hard, inner teeth are not eccentric with respect to the inner circumference of the barrel. No step is possibly defined between the inner circumference of the barrel and the upper inner peripheries of the hard, inner teeth. Hence, even though a portion of the chips may enter the interior of the barrel, it is very unlikely that such chips may be jammed in between the annular cutter and the core. Such chips can thus be guided within the barrel without applying any resistance thereto. Accordingly, even when a part of the chips enters the barrel, it is possible to prevent an increase in frictional resistance and generation of heat of friction, thus avoiding an increase in the load upon the electric drill or generation of heat in the annular cutter per se. Thus, it is possible to prevent the barrel from breaking down and the hard teeth from chipping.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An annular hole cutter comprising:
a substantially cylindrical barrel (1) having an outer and inner circumferential surface (3, 4), and an upper end and a lower end, said outer and inner circumferential surfaces being concentric;
a shank (2) attached to the upper end of said barrel, the central axis of the outer and inner circumferential surfaces (3, 4) of the barrel being in concentric relationship with the central axis of said shank; and
a plurality of circumferentially equidistantly spaced cutting teeth (5) formed of hard material attached to said lower end of said barrel, said cutting teeth (5) including outer cutting edges (8) and inner cutting edges (9), said outer cutting edges having an outer circumference the central axis of which is in concentric axial relationship relative to the outer and inner circumferential surfaces (3, 4) of said barrel (1), said cutting teeth (5) having varying radial thickness so that a center of an imaginary circle circumscribed by the inner peripheries of the inner cutting edges (9) of said cutting teeth is offset a short radial distance from the central axis of the outer and inner circumferential surfaces (3, 4) of said barrel, the inner peripheral surfaces (12) of the upper portions of the inner cutting edges (9) of said cutting teeth where the teeth are secured to said cylindrical barrel (1) being flush with the inner circumferential surface (4) of said barrel, the inner cutting edges (9) of a plurality of relatively thick cutting teeth (5) projecting farther radially inwardly from the inner circumferential surface (4) of said barrel than inner cutting edges (9) of a plurality of relatively thin cutting teeth so that said inner cutting edges (9) of the relatively thick cutting teeth (5) are formed with steps (12a) between the inner peripheral surfaces of the lower portions of the inner cutting edges (9) and the inner peripheral surfaces (12) of the upper portions of the inner cutting edges (9), said steps (12a) having a width corresponding to said radial offset distance, whereby a gap (15) is formed between the inner peripheral surfaces (12) of the upper portions of the inner cutting edges (9) extending above said steps (12a) and a core (14) in a workpiece being cut by the inner cutting edges wherein the majority of chips formed by said cutting teeth are normally discharged from said annular hole cutter and a portion of the chips ascending along the inner circumference (4) enter into said gap (15) to avoid jamming of the chips.

2. An annular hole cutter according to claim 1, wherein five cutting teeth are regularly spaced around the lower portion of said barrel.

3. An annular hole cutter according to claim 1, and further including lands extending upwardly of said teeth at a predetermined angle of convolution in a spiral direction.

* * * * *